United States Patent
Chung et al.

(10) Patent No.: US 6,538,030 B2
(45) Date of Patent: Mar. 25, 2003

(54) TREATING RADIATION FIBROSIS

(75) Inventors: Yih-Lin Chung, 3F, No. 18, Lane 160, Ssu-Wei Rd., Ta-An District, Taipei (TW); Rong-Lang Yen, No. 810, Chung-Chen Rd., Yung-Kung City, Tainan Hsien (TW); Ae-June Wang, Hsinchu (TW); Lin-Fen Yao, Hsinchu (TW)

(73) Assignees: Yih-Lin Chung, Taipei (TW); Rong-Lang Yen, Tainan Hsien (TW)

( * ) Notice: Subject to any disclaimer, the term of this patent is extended or adjusted under 35 U.S.C. 154(b) by 0 days.

(21) Appl. No.: 09/938,926

(22) Filed: Aug. 24, 2001

(65) Prior Publication Data

US 2002/0055542 A1 May 9, 2002

(30) Foreign Application Priority Data

Sep. 20, 2000 (TW) ........................... 89119330 A

(51) Int. Cl.⁷ ............................... A61K 31/192
(52) U.S. Cl. ...................................... 514/570
(58) Field of Search ........................ 514/570

(56) References Cited

U.S. PATENT DOCUMENTS

| | | | |
|---|---|---|---|
| 5,605,930 A | | 2/1997 | Samid ................ 514/510 |
| 5,939,455 A | * | 8/1999 | Rephaeli ............. 514/547 |
| 6,037,376 A | | 3/2000 | Samid ................ 514/568 |

FOREIGN PATENT DOCUMENTS

| | | | |
|---|---|---|---|
| WO | 98/58685 | * | 12/1998 |
| WO | 99/63982 | * | 12/1999 |

OTHER PUBLICATIONS

*Involvement Of The Cyclin–Dependent Kinase Inhibitor p16 (INK4a)In Replicative Senescence Of Normal Human Fibroblasts* by D. A. Alcorta, Y. Xiong, D. Phelps, G. Hannon, D. Beach, and J. C. Barrett. Proc Natl Adam Sci USA, Nov.

*Inhibition Of Proliferation And Induction Of Differentiation In Medulloblastoma– And Astrocytoma–Derived Cell Lines With Phenylacetate* by G. Stockhammer, G. T. Manley, R. Johnson, M. K. Rosenblum, D. Samid, and F. S. Liberman. Journal of Neurosurgery. 83(4):672–81, Oct. 1995.

*Phenylbutyrate (PB) For Refractory Solid Tumors: A Phase I Clinical And Pharmacological Evaluation (Meeting Abstract)* by M. Carducci, M. Bowling, M. Eisenberger, V. Sinibaldi, J. Simons, T. Chen, D. Noe, L. Grochow, and R. Donehower. Anticancer Research, 17:3921–3982 (1997).

*Therapeutic Targeting of Transcription in Acute Promyelocytic Leukemia by Use of an Inhibitor of Histone Deacetylase* by R. P. Warrell, L–Z. He, V. Richon, E. Calleja, and P. R. Pandolfi. Journal of the National Cancer Institute, vol. 90, No. 21, Nov. 4, 1998.

*A Novel Approach for Nasopharyngeal Carcinoma Treatment Uses Phenylbutyrate as a Protein Kinase C Modulator: Implications for Radiosensitization and EBV–targeted Therapy* by Y–L. Chung, Y–H. Wu Lee, S–H. Yen, and K–H Chi. Clinical Cancer Research, vol. 6, 1452–1458, Apr. 2000.

*Pharmacological Manipulation Of Gene Expression Brings New Hope to The Treatment Of X–Linked Adrenoleukodystrophy* by Ronald J. A. Wanders. Nature Medicine, vol. 4, No. 11, Nov. 1998.

* cited by examiner

*Primary Examiner*—Phyllis G. Spivack
(74) *Attorney, Agent, or Firm*—Fish & Richardson P.C.

(57) ABSTRACT

A method for treating a subject having radiation fibrosis is disclosed comprising topically administrating to the subject an effective amount of a compound of the formula:

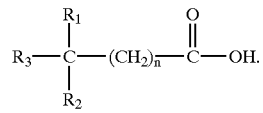

$R_1$ and $R_2$, independently, is H or $C_1$~$C_6$ alkyl; $R_3$ is aryl or heteroaryl; and n is 0, 1, 2, 3, 4, 5, or 6.

12 Claims, No Drawings

TREATING RADIATION FIBROSIS

BACKGROUND

Phenylbutyrate, an aromatic fatty acid, can be purified from a biological sample (e.g., mammalian urine or plasma) or chemically synthesized. Sodium phenylbutyrate has been approved by the U.S. Food and Drug Administration as an orphan drug for treating hyperammonemia (Samid et al. (1992) *Cancer Res.* 52: 1988–1992). It has also been clinically used in patients with in-born genetic errors which lead to liver failure or urea cycle disorders.

Radiation fibrosis, a local defect, is a frequent sequela of therapeutic or accidental radiation overexposure of normal tissues. It results from a complex tissue repair response whose predominant characteristics are massive deposition of extracellular matrix and excessive fibroblast proliferation. An ulcer is also a local defect, i.e., excavation of the surface of an organ or tissue. There is a need for effective treatment of both disorders.

SUMMARY

The present invention is based on the unexpected discovery that certain aromatic fatty acids can be used to effectively treat an ulcer and radiation fibrosis.

Thus, this invention features a method for treating a subject having an ulcer or radiation fibrosis. The method includes topically administrating to the subject an effective amount of a compound and a pharmaceutically acceptable carrier. The compound, which can be synthesized by well-known methods or purchased from commercial suppliers, has the following formula:

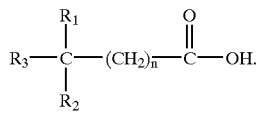

$R_1$ and $R_2$, independently, is H or $C_1$–$C_6$ alkyl; $R_3$ is aryl or heteroaryl; and n is 0, 1, 2, 3, 4, 5, or 6. A subset of the compounds encompassed by the above formula are featured by that $R_3$ is phenyl, n is 0, 1, or 2, and each of $R_1$ and $R_2$, independently, is H, methyl, or ethyl. Three exemplary compounds are 2-phenylbutyrate, 3-phenylbutyrate, and 4-phenylbutyrate.

Alkyl, aryl, and heteroaryl mentioned above include both substituted and unsubstituted moieties. The term "substituted" refers to one or more substituents (which may be the same or different), each in replace of a hydrogen atom. Examples of substituents include, but are not limited to, halogen, amino, hydroxyl, mercapto, cyano, $C_1$–$C_6$ alkyl, $C_1$–$C_6$ alkenyl, $C_1$–$C_6$ alkoxy, aryl, heteroaryl, or heterocyclyl, wherein alkyl, alkenyl, alkoxy, aryl, heteroaryl, and heterocyclyl are optionally substituted with $C_1$–$C_6$ alkyl, halogen, amino, hydroxyl, mercapto, cyano. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, pyridinyl, carbozolyl, and indolyl.

The term "aromatic fatty acids" used herein refers to all the compounds covered by the above formula, and includes the compounds themselves, as well as their salts and their prodrugs, if applicable. Such salts, for example, can be formed between a negatively charged substituent (e.g., carboxylate) on an aromatic fatty acid compound and a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the aromatic fatty acids described above. As used herein, the term "treatment" refers to administration of a topical composition to a subject with the purpose to cure, heal, alleviate, relieve, remedy, ameliorate, improve or prevent an ulcer or radiation fibrosis, its symptoms or the predisposition toward it.

Also within the scope of this invention is the use of the above-described compounds for the manufacture of a medicament for the treatment of an ulcer or radiation fibrosis.

Other features or advantages of the present invention will be apparent from the following detailed description of several embodiments, and also from the appending claims.

DETAILED DESCRIPTION

One aspect of this invention is a method for treating a subject having an ulcer or radiation fibrosis by using a topical composition that contains an effective amount of one or more aromatic fatty acids described above and a pharmaceutically acceptable carrier.

An effective amount of an aromatic fatty acid is the amount of the compound which, upon administration to a subject in need of treatment or prophylaxis of an ulcer or radiation fibrosis, is required to confer therapeutic effect on the treated subject. It may range from 0.1% to 40% (e.g., 0.1% to 10%) by weight of a topical composition. As recognized by those skilled in the art, the effective doses vary depending on route of administration, excipient usage, and the possibility of co-usage with other therapeutic treatments such as the use of other anti-ulcer or anti-radiation fibrosis agents. Effective amounts and treatment regimens for any particular subject (e.g., human, dog, or cat) will also depend upon a variety of other factors, including the activity of the specific compound employed, the age, body weight, general health status, sex, diet, time of administration, rate of excretion, the severity and course of the disease, and the patient's disposition to the disease.

A pharmaceutically acceptable carrier may include water, a solvent, an emollient, a surfactant, a preservative, or a combination thereof. Water, when present, can be in an amount of 5 to 95% by weight. Other than water, the biological acceptable carrier can also contain a relatively volatile solvent such as a monohydric $C_1$–$C_3$ alkanol (e.g., methyl alcohol or ethyl alcohol) in an amount of 1 to 70% by weight, and an emollient such as those in the form of silicone oils and synthetic esters in an amount of 0.1 to 30% by weight. Anionic, nonionic, or cationic surfactants may also be included in the biological acceptable carrier. The concentration of total surfactants may be from 0.1 to 40% by weight. Examples of anionic surfactants include soap, alkyl ether sulfate and sulfonate, alkyl sulfate and sulfonate, alkylbenzene sulfonate, alkyl and dialkyl sulfosuccinate, $C_1$–$C_2$, acyl isethionate, acyl glutamate, $C_8$–$C_{20}$ alkyl ether phosphate, and a combination thereof Examples of nonionic surfactants include $C_{10}$–$C_{20}$ fatty alcohol or acid hydrophobe condensed with from 2 to 100 moles of ethylene oxide or propylene oxide per mole of hydrophobe; $C_2$ to $C_{10}$ alkyl phenol condensed with from 2 to 20 moles of alkylene oxide; mono and di- fatty acid ester of ethylene glycol; fatty acid monoglyceride; sobitan, mono- and di-$C_8$ to $C_{20}$ fatty acid; block co-polymer (ethylene oxide/propylene oxide); polyoxyethylene sorbitan, and a combination thereof. Preservatives may also be included in the biological acceptable carrier to prevent growth of potentially harmful microorganisms, and may be employed in an amount of 0.01 to 2% by weight. Examples of preservatives include alkyl ester of para-hydroxybenzoic acid, hydantoin derivative, propionate salt, and a variety of quaternary ammonium compounds. Each preservative should be selected based on its compatibility with other ingredients in the topical composition.

A topical composition for practicing this invention may be provided as an aqueous, anhydrous or emulsion-like formulation, such as oil, cream, spray (aerosol or non-aerosol), gel (oral or non-oral), or ointment. When an anhydrous formulation is desired, various forms may be adopted, e.g., sticks, roll-ons, adhesive patches, or overnight masks. Peelable masks can be formulated by placing the composition as a gel or paste on a protective layer made of a film-forming polymer (e.g., polyvinyl alcohol) and an adhesive promoting polymer (e.g., hydrophobic acrylate or methacrylate polymer, such as Pemulen TR2.RTM. from the B. F. Goodrich Company).

An example of such a topical composition used for treating an ulcer or radiation fibrosis is an ointment. An ointment composition can be formulated with an aromatic fatty acid suspended or dissolved in a carrier, such as mineral oil, liquid petroleum, white petroleum, propylene glycol, polyoxyethylene polyoxypropylene compound, emulsifying wax, water, sorbitan monostearate, polysorbate 60, cetyl esters wax, cetyl alcohol, 2-octyldodecanol, and stearyl alcohol. The topical composition can also be a sustained release formulation (e.g., a patch) for delivering an aromatic fatty acid over an extended period of time. Another example of the topical composition is oral gel, which can be particularly used in the oral mucosa. The oral gel can include a viscose-enhancing agent (such as sodium polyacrylate) and an aromatic fatty acid ranging from 0.1% to 10% by weight. A further example of the topical composition is a liposomal composition in which an aromatic fatty acid is encapsulated in liposomes. As well known in the art, liposomes are generally derived from phospholipids or other lipid substances. Liposome compositions are formed by mono-or multilamellar hydrated liquid crystals, which are dispersed in an aqueous medium. Any non-toxic, pharmaceutically acceptable, and metabolizable lipid capable of forming liposomes can be used. A composition in liposome form can contain, in addition to an aromatic fatty acid, stabilizers, excipients, and preservatives. Examples of lipid substances include, but are not limited to, cholesterol, phospholipids, and phosphatidylcholines. Methods for forming liposomes are known in the art as described, for example, in Prescott, Ed., Methods in Cell Biology, Volume XIV, Academic Press, New York, N.Y. (1976), pp. 33.

Other than topical administration, a pharmaceutical composition containing an aromatic fatty acid may be administered with a pharmaceutically acceptable carrier to a subject orally, parenterally, sublingually, rectally, enterally, or by pulmonary absorption. The pharmaceutical composition can be used for treating an ulcer or radiation fibrosis. Examples of parenteral dosage forms include aqueous solutions, isotonic saline or 5% glucose of the active agent, or other well-known pharmaceutically acceptable excipient. Solubilizing agents such as cyclodextrans or other solubilizing agents well-known to those familiar with the art, can be utilized as pharmaceutical excipients for delivery of the aromatic fatty acids. The pharmaceutical composition can be formulated into dosage forms, such as a capsule, a gel seal, or a tablet for oral administration, or other types of formulations for other routes of administration. Capsules may contain any standard pharmaceutically acceptable materials such as gelatin or cellulose. Tablets, on the other hand, may be formulated in accordance with conventional procedures by compressing mixtures of an aromatic fatty acid with a solid carrier and a lubricant. Examples of solid carriers include starch and sugar bentonite.

In order that the invention described herein may be more readily understood, the following examples are set forth. It should be understood that these examples are for illustrative purposes only and are not to be construed as limiting this invention in any manner. All references cited herein are expressly incorporated by reference in their entirety.

EXAMPLE 1

Various Topical Compositions—Oleaginous Ointment, Cream and Gel

A. Preparation of an Oleaginous Ointment (Tri-o-01):

470 g of white petrolatum (Riedel-de Haen), 25 g of paraffin wax 50/52 (local company), and 5 g of 4-phenylbutyrate (Merck) were mixed in a beaker and heated at 70° C. to form a paste. The paste was stirred at 400 rpm for 1 hour, and then cooled at room temperature.

B. Preparalion of an Oleaginous Ointment (Tri-o-07):

65 g of white petrolatum (Riedel-de Haen), 15 g of cetyl alcohol (Riedel-de Haen), 260 g of sofi paraffin (Merck), 155 g of liquid paraffin (Merck), and 5 g of 4-phenylbutyrate (Merck) were mixed in a beaker and heated at 70° C. to form a paste. The paste was stirred at 400 rpm for 1 hour, and then cooled at room temperature.

C. Preparation of Cream (Tri-c-02–3).

Part I: 70 g of Tefose 63®, 20 g of Superpolystate®, 10 g of Coster 5000®, 15 g of Myriyol 318®, 15 g of Coster 5088®, and 15 g of GMS SE® (all commercially available from local company) were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), and 149.061 g of deionized water were mixed in a beaker and heated at 70° C.

The part II was slowly added into the part I and continually stirred at 400 rpm for 5 minutes to form a mixture. 2% Stabileze QM® (prepared by dissolving 2 g of Stabileze QM® in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

D. Preparation of Gel (Tri-g-01–2):

Part I: 10 g of Stabileze QM® and 232.035 g of deionized water were mixted in a beaker and heated at 70° C.

Part II: 5.739 g of sodium 4-phenylbutyrate (Triple Crown America, Inc.), 0.125 g of methylparaben (Merck), 0.075 g of propylparaben (Merck), 232.035 g of deionized water, and 20 g of 10%NaOH were mixed in a beaker and heated at 70° C.

The part II was slowly added into the part I and continually stirred with 400 rpm for 20 minutes to form a mixture. The mixture was cooled at room temperature.

E. Preparation of Gel (Tri-g-05–1):

Part I: 10 g of Stabileze QM® and 380.561 g of deionized water were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), 83.5 g of 1,2-propandiol, and 20 g of 10%NaOH were mixed in a beaker and heated at 70° C.

The part II was slowly added into the part I and continually stirred at 400 rpm for 20 minutes to form a mixture. The mixture was cooled at room temperature.

F. Skin Permeation Test:

Each composition prepared above was filled into the upper panel of a Modified Franz diffusion cell (9-mm diameter, 6.4-mL volume, PMC DATAPLATE). A stirrer was placed and 6.4 mL of degassed receptor solution (phosphate buffer saline) pre-heated to 32±0.5° C. was poured into the lower panel, avoiding bubble formation. A 0.45-$\mu$m filter (Hydrophobic Durapore Membrane, Millipore) was placed between upper and lower panels and clipped.

The skin (purchased from Ohio Valley Tissue & Skin Center) was thawed at room temperature. The thawed skin was placed in a 60° C. thermostatic water bath. The stratum corneum and dermis were separated by forceps, and stored.

The Modified Franz diffusion cell was placed in a 32±0.5° C. thermostatic chamber with stirring. Each composition was sampled 6.4 mL at 1, 2, 3, 4, 6 and 8 hours, followed by filtrating with a 0.45-$\mu$m filter. After each sampling, 6.4 mL of receptor solution pre-heated to 32° C. was added to the cell to maintain constant volume. The amount of phenylbutyrate in each sample was analyzed by HPLC (Jasco). The permeation amount was calculated by the following formula:

permeation amount ($\mu$g)=(sample conc. ×6.4)/0.636

The sample concentration is the analytic result from HPLC ($\mu$g/mL); constant 6.4 represents the volume of the diffusioncell (cm$^3$); and constant 0.636 represents the area of the skin (cm$^2$). The results are shown in Table 1.

phase (acetonitrile: 0.02 M KH$_2$PO$_4$=3:7) to a total volume of 20 mL, filtrated (0.45 $\mu$m), and analyzed by HPLC.

(2) For cream and gel: To 25 mL acetonitrile in a 50-mL bottle was added 0.5 g of a sample, and sonicated for 30 minutes to form a mixture. The mixture was cooled at room temperature. 2 mL of the mixture was diluted with 0.02 M KH$_2$PO$_4$ to a total volume of 20 mL. 5 mL of the just-obtained solution was further diluted with mobile phase to a total volume of 20 mL, filtrated (0.45 $\mu$m), and analyzed by HPLC.

The results showed that the appearance of each composition remained the same after 6 months. HPLC analyses showed that the amounts of phenylbutyrate in the compositions remained the same, except that the amount of phenylbutyrate in Tri-o-07 was dropped from 95% to 80% after 6 months in conditions of 75% RH along with 35° C. and 40° C.

According to the above results, the shelf life of each composition at room temperature was calculated according to the ARRHENIUS EQUATION:

$$Ln(K \times 1000) = A + B \times (1000/T)$$

wherein K is the rate constant; A is intercept; B is slope; and T is absolute temperature (° k).

The result is shown in Table 2, wherein the shelf life of the composition Tri-c-02–3 composition was unexpected as long as 83.9 months.

TABLE 1

Permeation test of formulations containing 1% 4-phenylbutyrate

| Sampling Time | Cumulated Permeation Amount ($\mu$g) | | | | |
|---|---|---|---|---|---|
| (hr) | Tri-o-01 | Tri-o-07 | Tri-c-02-3 | Tri-g-01-2 | Tri-g-05-1 |
| 1 | 46.4 ± 12.9 | 42.8 ± 9.2 | 17.9 ± 7.3 | 133.2 ± 22.6 | 55.1 ± 12.4 |
| 2 | 796.0 ± 334.3 | 523.5 ± 146.9 | 248.8 ± 68.9 | 1005.4 ± 89.7 | 530.5 ± 40.6 |
| 3 | 1464.9 ± 487.3 | 948.4 ± 242.6 | 457.6 ± 106.4 | 1880.2 ± 166.0 | 1038.5 ± 232.2 |
| 4 | 1834.9 ± 612.7 | 1322.8 ± 254.3 | 701.1 ± 201.9 | 2018.8 ± 163.5 | 1087.1 ± 229.2 |
| 6 | 1865.3 ± 635.5 | 1389.6 ± 247.3 | 745.9 ± 218.6 | 2235.5 ± 178.4 | 1187.9 ± 255.0 |
| 8 | 1924.6 ± 641.5 | 1453.9 ± 243.5 | 804.0 ± 250.9 | 2377.0 ± 199.3 | 1273.7 ± 261.6 |

The result shown in Table 1 indicates that all five compositions were readily permeable through the stratum corneum, and high permeation can be achieved at the 1-hour stage. The Tri-g-01–2 composition was the most permeable.

G. Stability Test:

The stability test of each composition prepared above was conducted according to three accelerated conditions, including 75% RH along with 30° C., 35° C., and 40° C., respectively. Each composition was sampled at 0, 1, 2, 3, 4, 5, and 6 months. The extraction methods follow:

(1) For an oleaginous ointment: To 25 mL acetonitrile in a 50-mL bottle was added 0.5 g of a sample, and sonicated at 60° C. for 30 minutes to form a mixture. The mixture was cooled at room temperature. 2 mL of the mixture was diluted with 0.02 M KH$_2$PO$_4$ to a total volume of 20 mL. 5 mL of the just-obtained solution was further diluted with a mobile

TABLE 2

The calculated shelf life of formulations containing 1% 4-phenylbutyrate

| Formulation | Shelf Life (month) |
|---|---|
| Tri-o-01 | 2.0 |
| Tri-o-07 | 6.1 |
| Tri-c-02-3 | 83.9 |
| Tri-g-01-2 | 10.8 |
| Tri-g-05-1 | 23.9 |

I. Pharmacokinetics study:

An in vivo drug concentration was calculated based on the model described in Young, Mu Jen, et al., "Mathematical Modeling of Matrix Type Transdermal Therapeutic System", (1994) 21$^{st}$ CRS Annual Meeting on Controlled Delivery of Drug and Bioactive Materials, Nice France. This model assumes that: (1) the permeation of drugs through skin is dependent on Fick's Diffusion Law; (2) the permeation amount of drugs does not change with time; (3) the diffusion rate through the stratum corneum is constant; (4) the drugs are assimilated into the bloodstream after entering the dermis; and (5) the skin contains no drugs when the test starts. The pharmacokinetics calculation results are shown in Table 3.

TABLE 3

Results of pharmacokinetics study

| Sampling | Cumulated Permeation Amount ($\mu$g) | | | | |
|---|---|---|---|---|---|
| Time (hr) | Tri-o-01 | Tri-o-07 | Tri-c-02-3 | Tri-g-01-2 | Tri-g-05-1 |
| 1 | 46.4 | 42.8 | 17.9 | 133.2 | 55.1 |
| 2 | 796 | 523.5 | 248.8 | 1005.4 | 530.5 |
| 3 | 1464.9 | 948.4 | 457.6 | 1880.2 | 1038.5 |
| 4 | 1834.9 | 1322.8 | 701.1 | 2018.8 | 1087.1 |
| 6 | 1865.3 | 1389.6 | 745.9 | 2235.5 | 1187.9 |
| 8 | 1924.6 | 1453.9 | 804 | 2377 | 1273.7 |
| Slope | 709.25 | 452.8 | 219.85 | 873.5 | 491.7 |
| Intercept | −649.4 | −400.7 | −198.2667 | −740.7333 | −442.0333 |
| Retention time | 0.916 | 0.885 | 0.902 | 0.848 | 0.899 |
| D | 1.16E−05 | 1.21E−05 | 1.18E−05 | 1.26E−05 | 1.19E−05 |
| Cs | 4.87E+08 | 3.01E+08 | 1.49E+08 | 5.56E+08 | 3.32E+08 |
| mg/cm$^2$ | 1.9482 | 1.2021 | 0.5948 | 2.2222 | 1.3261 |

The parameters in Table 3 are: (1) slope, indicating the permeation amount of each drug through skin per hour (mg/cm$^2$/hr); (2) intercept, a negative number indicating the potential permeation amount of each drug through skin (a positive number indicating that the sampling time is too long to obtain an accurate value); (3) retention time, the average time (hr) that each drug permeates skin; (4) D, a drug diffusion constant (cm$^2$/s); (5) Cs, a drug concentration on skin ($\mu$g/cm$^3$); and (6) mg/cm$^2$, the permeation amount of drugs through per cm$^2$ skin. The results show the Tri-g-01–2 composition has the strongest ability to permeate skin.

EXAMPLE 2

A Topical Composition for Use in a Sustained Release Formulation (e.g., a Patch)

A: Preparation (Tri-s-04 and Tri-s-05):

Two formulations were prepared according to the compositions listed in the Table 4.

TABLE 4

Compositions of two sustained release formulations

| | No. of formulation | |
|---|---|---|
| Composition | Tri-s-04 | Tri-s-05 |
| PF-127 ®(BASF Inc.)* | 2 | 4 |
| Sodium carboxy-methylcellulose* | 12 | 12 |
| Deionized water | 82.8523 | 80.8523 |
| Sodium 4-phenylbutryate | 1.1477 | 1.1477 |
| 85% phosphoric acid | 2 | 2 |
| pH | 5.93 | 6.01 |

*PF-127 ® is the base of the compositions, and sodium carboxymethylcellulose is a thickening agent.

B. Stability test:

The stability test of the formulations prepared above was conducted under accelerated condition of 75% RH with 40° C. for 3 months. The results show that both Tri-s-04 and Tri-s-05 compositions form a uniform semisolid, yellow-white in color.

C. Permeation test.

The skin permeation test of both Tri-s-04 and Tri-s-05 compositions was conducted according to the method described in Example 1 (skin No. 0415000103), with the gel composition Tri-g-05–1 composition as control group. Each composition was sampled at 0.33, 0.66, 1, 2, 3, 4, 6, 8 and 24 hours, and the cumulated permeation amounts were calculated. The results are shown in Table 5.

TABLE 5

Permeation test of two sustained release formulation

| Sampling | Cumulated Permeation Amount ($\mu$g) | | |
|---|---|---|---|
| Time (hr) | Tri-s-04 | Tri-s-05 | Tri-g-05-1 |
| 0.33 | 43.8 ± 8.4 | 24.1 ± 7.8 | 31.2 ± 6.6 |
| 0.66 | 101.2 ± 18.2 | 60.7 ± 17.4 | 75.8 ± 14.7 |
| 1 | 145.0 ± 21.4 | 94.4 ± 26.0 | 116.1 ± 23.0 |
| 2 | 296.1 ± 40.6 | 195.2 ± 48.2 | 222.8 ± 40.6 |
| 3 | 420.0 ± 55.8 | 287.7 ± 71.6 | 308.3 ± 51.1 |
| 4 | 512.8 ± 65.9 | 363.0 ± 82.1 | 369.9 ± 57.7 |
| 6 | 719.7 ± 82.7 | 518.7 ± 116.3 | 489.1 ± 70.9 |
| 8 | 787.6 ± 95.0 | 659.2 ± 137.6 | 578.5 ± 76.0 |
| 24 | 1557.0 ± 68.5 | 1292.6 ± 168.5 | 925.2 ± 101.5 |

D. Pharmacokinetics study:

The pharmacokinetics test of both Tri-s-04 and Tri-s-05 compositions was conducted according to the method described in Example 1 to calculate the in vivo drug concentration at each time period. The results are shown in Table 6.

TABLE 6

Results of pharmacodynamics study

| Sampling | Cumulated Permeation Amount ($\mu$g) | | |
|---|---|---|---|
| Time (hr) | Tri-s-04 | Tri-s-05 | Tri-g-05-1 |
| 0.33 | 43.8 | 24.1 | 31.2 |
| 0.66 | 101.2 | 60.7 | 75.8 |
| 1 | 145 | 94.4 | 116.1 |
| 2 | 296.1 | 195.2 | 222.8 |
| 3 | 420 | 287.7 | 308.3 |
| 4 | 512.8 | 363 | 369.9 |
| 6 | 719.7 | 518.7 | 489.1 |
| 8 | 878.6 | 659.2 | 578.5 |
| 24 | 1557 | 1292.6 | 925.2 |
| Slope | 149.848637 | 102.1206 | 113.5819 |
| Intercept | −3.28617525 | −8.49509 | −2.07846 |
| Retention time | 0.02 | 0.083 | 0.018 |
| D | 4.86E−0 | 1.28E−04 | 5.83E−04 |
| Cs | 2.46E+0 | 6.37E+06 | 1.56E+06 |
| mg/cm$^2$ | 0.009 | 0.025485 | 0.0062 |

EXAMPLE 3

A Topical Composition—Oral Gel

A. Preparation (Tri-oral-04):

345 g of white petrolatum (Riedel-de Haen), 150 g of sodium polyacrylate (as a viscose-enhancing agent), and 5 g of 4-phenylbutyrate (Merck) were mixed in a beaker and heated at 70 ° C. to form a paste. The paste was stirred at 400 rpm for 1 hour.

B. Stability Test:

The stability test of composition Tri-oral-04 was conducted under accelerated condition of 75% RH at 40° C. for 3 months. The results show that the Tri-oral-04 composition forms a white semisolid with granules, and without separation of oil and water. This composition is useful in the application of oral gel.

EXAMPLE 4

A Topical Liposomal Composition
A. Preparation

In this liposomal formulation, egg phosphatidylcholine (EPC) and cholesterol were used in equi- or different-molar concentrations as primary lipid components. Various liposome located with 4-phenylbutyrate were obtained by varying the lipid:phenylbutyrate ratio. Liposomes were prepared by thin film hydration, sized by membrane extrusion, and physically evaluated.

B. Stability Test.

Both vesicle particle size and encapsulation efficiency was shown to be important indicators of the physical stability of the liposomal products. The particle size of all phenylbutyrate-containing liposomes increased over 30 days from 100–120 nm to 150–200 nm at 37° C. A composition containing high lipid concentration and high phenylbutyrate loading had greater increase in particle size. Lower temperature had a less pronounced effect on the particle size increment. The particle size of liposomes at 4° C. showed negligible change over 60 days. The encapsulation efficiency was high for 0.5%–2% phenylbutyrate liposomes with EPC:cholesterol molar ratio of 1:1 remained so for 10 days, from approximately 97±2% to 92±2% determined by HPLC assay.

EXAMPLE 5

Treatment of Skin Ulcer

Two groups of 5 Long Evans rats, weighing 150±20 g, were used (Winter et al. (1966) *Arthritis Rheum.* 9: 394–404). One group of rats were topically treated with the Tri-c-02–3 composition at a dose of 200 mg/paw, twice daily for 18 consecutive days. The other group of rats (control) were treated with a placebo. A well-ground suspension of killed *Mycobacterium tuberculosis* (DIFCO, USA; 0.3 mg in 0.1 ml of light mineral oil; Complete Freund's Adjuvant, CFA) was administered into the subplantar region of the right hind paw of each rat to develop skin ulcer and joint swelling immediately after first dosing on the first day (denoted day 1). The hind paw volume was measured by Plethsmometer (Cat. No. 7150, UGO BASILE, Italy) and Water cell (25 mm diameter, Cat. No. 7157, UGO BASILE, Italy) on days 0 (before CFA treatment), and days 1, 5, 10, and 15 (after CFA treatment) of the right paw, and days 0, 14, and 18 (without CFA treatment) of the left paw. The rats were weighed just before the first dose and 1 hour after the final dose. The results show that the Tri-c-02–3 composition had significant therapeutic effects on skin ulcer. The results also show that swelling of the joint along with thenar ulcer was obvious in the rats treated with the placebo, while reduction of swelling was observed in the rats treated with the Tri-c-02–3 composition.

EXAMPLE 6

Treatment of Radiation Fibrosis

Adult female Sprague Dawley (SD) rats were purchased from the animal center of the National Science Council of Taiwan, and weighed 250–300 g at the time of irradiation. Each rat was caged alone and allowed chow and water. They were anesthetized with pentobarbital 50 mg/kg i.p. before irradiation. The skin over gluteal area was shaved completely and radiation fields with 2-cm diameter were outlined with a marking pen just prior to irradiation. An electron beam with 6 MeV energy produced by a linear accelerator was used. The dose was delivered on Day 0 at 4 Gy/min to the prepared area. Then either vehicle or the Tri-c-02–3 cream (50 mg/rat) was applied topically to the irradiated skin twice daily from Day 1 to Day 120. There were three groups animals (5 each): one group treated with skin irradiation followed by vehicle, another with skin irradiation followed by 1% of Tri-c-02–3, and the third with skin irradiation only. The gross skin reactions were evaluated in all rats, and 3 rats in each group underwent histological examination. Skin samples were taken on Day 130. Each specimen was embedded in a paraffin block and thin sections were prepared, stained by the hematoxylin eosin method and examined by two pathologists under a light microscope (40×and 200×).

Skin wounds healed quickly in the Tri-c-02–3 composition treated group since the second week, which could not be observed in the other two groups. On Day 130, skin samples taken from the Tri-c-02–3-treated group had softer and thinner demils and less capillary bleeding, while skin samples taken from the other two groups had rigid thick dernis and oozed easily.

It was observed that the rats of the vehicle treated group had thinner epidermis, and their dermis showed subepidermal edematous change, increased thickness due to more fibroblasts and collagen deposit, and higher density of proliferative neovessels and appendage. Scattered lymphocyte infiltration was also observed in the subcutaneous layer. A control group (irradiation only) had the thin epidermis and thick dermis similar to the vehicle-treated group. On the other hand, the Tri-02–3 composition-treated rats had thicker epidermis with more cell layers and the thickness and feature of dermis were almost the same as normal skin except scarce skin appendage.

The results indicate that Tri-c-02–3 composition has therapeutic effects not only on the radiation epidermis healing but also on the late sequela of radiation dermal fibrosis. The Tri-c-02–3 composiiton treated group has thicker epidermis with more cell layers but has thinner dermis (measured from epidermis to the subcutaneous fat layer) with less collagen deposition when compared to the vehicle and control groups.

EXAMPLE 7

Inhibition of Skin Ulcer

Twenty female BALB/c mice were inoculated with 1MEA7R1 cells. The cells ($5 \times 10^5$) in 1 mL phosphate buffered saline were injected subcutaneously into the flank area. The tumor size was allowed to grow up to the largest dimensions of about 0.5 cm. Skin ulcer developed concurrently with tumor growth. Twelve mice with the same tumor size were selected, and divided into two groups: the control group (6 mice; only ointment base was used); and the treated group (6 mice; adequate amount of the Tri-o-01 composition was applied topically to the tumor sites, twice per day for four weeks). It was observed that skin ulcer in the treated group developed much slower than that in the control. Further, withdrawing of the Tri-o-01 composition treatment resulted in loss of skin ulcer inhibition.

OTHER EMBODIMENTS

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to aromatic fatty acids described above can also be used to practice the present invention. Thus, other embodiments are also within the claims.

What is claimed is:

1. A method for treating a subject having radiation fibrosis, comprising topically administrating to the subject an effective amount of a compound and a pharmaceutically acceptable carrier, in which the compound has the formula:

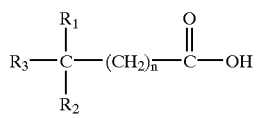

wherein $R_1$ and $R_2$, independently, is H or $C_1$~$C_6$ alkyl;

$R_3$ is aryl or heteroaryl; and n is 0, 1, 2, 3, 4, 5, or 6.

2. The method of claim 1, wherein $R_3$ is aryl.
3. The method of claim 2, wherein $R_3$ is phenyl.
4. The method of claim 1, wherein n is 0.
5. The method of claim 4, wherein $R_3$ is phenyl.
6. The method of claims 5, wherein one of $R_1$ and $R_2$ is H, and the other is ethyl.
7. The method of claim 1, wherein n is 1.
8. The method of claim 7, wherein $R_3$ is phenyl.
9. The method of claim 8, wherein one of $R_1$ and $R_2$ is H, the other is methyl.
10. The method of claim 1, wherein n is 2.
11. The method of claim 10, wherein $R_3$ is phenyl.
12. The method of claim 11, wherein each of $R_1$ and $R_2$ is H.

* * * * *